(12) United States Patent
Clarke

(10) Patent No.: US 8,772,309 B2
(45) Date of Patent: Jul. 8, 2014

(54) PHARMACEUTICAL FORMULATION OF APOMORPHINE FOR BUCCAL ADMINISTRATION

(71) Applicant: Amarin Pharmaceuticals Ireland Limited, Dublin (IE)

(72) Inventor: Anthony Clarke, Checkendon (GB)

(73) Assignee: Amarin Pharmaceuticals Ireland Limited, Ballsbridge (IE)

( * ) Notice: Subject to any disclaimer, the term of this patent is extended or adjusted under 35 U.S.C. 154(b) by 0 days.

(21) Appl. No.: 13/669,148

(22) Filed: Nov. 5, 2012

(65) Prior Publication Data

US 2013/0131098 A1 May 23, 2013

Related U.S. Application Data

(63) Continuation of application No. 11/919,799, filed as application No. PCT/GB2006/001665 on May 8, 2006, now abandoned.

(30) Foreign Application Priority Data

May 6, 2005 (GB) .................................... 0509317.4

(51) Int. Cl.
*A01N 43/42* (2006.01)
*A61K 31/44* (2006.01)

(52) U.S. Cl.
USPC ........................................................ 514/284

(58) Field of Classification Search
USPC .......................................................... 514/284
See application file for complete search history.

(56) References Cited

FOREIGN PATENT DOCUMENTS

WO    WO98/48784    * 11/1998 ............... A61K 9/22

OTHER PUBLICATIONS

Burkman, A. M., Some Kinetic and Thermodynamic Characteristics of Apomorphine Degradation, 1965, Journal of Pharmaceutical Sciences, vol. 54, Issue 2, pp. 325-326.*
Panegyres et al, Sublingual Apomorphine Solution in Parkinson's Disease, 1991, The Medical Journal of Australia, vol. 155, pp. 371-374.*

* cited by examiner

*Primary Examiner* — Trevor Love
(74) *Attorney, Agent, or Firm* — Dickinson Wright PLLC

(57) ABSTRACT

The present invention provides a kit comprising, in separate compartments of a container, the following components (a) and (b): (a) a combination of apomorphine or a pharmaceutically acceptable acid addition salt thereof and a pharmaceutically acceptable excipient or carrier; and (b) a solution which comprises a diluent and a pH modifying agent; the components being presented such that they can be combined at the point of use into a formulation which is adjusted to a pH ranging from mildly acidic to alkaline and which is suitable for buccal administration. The formulation is useful in treating Parkinson's disease and in promoting sexual function.

5 Claims, 1 Drawing Sheet

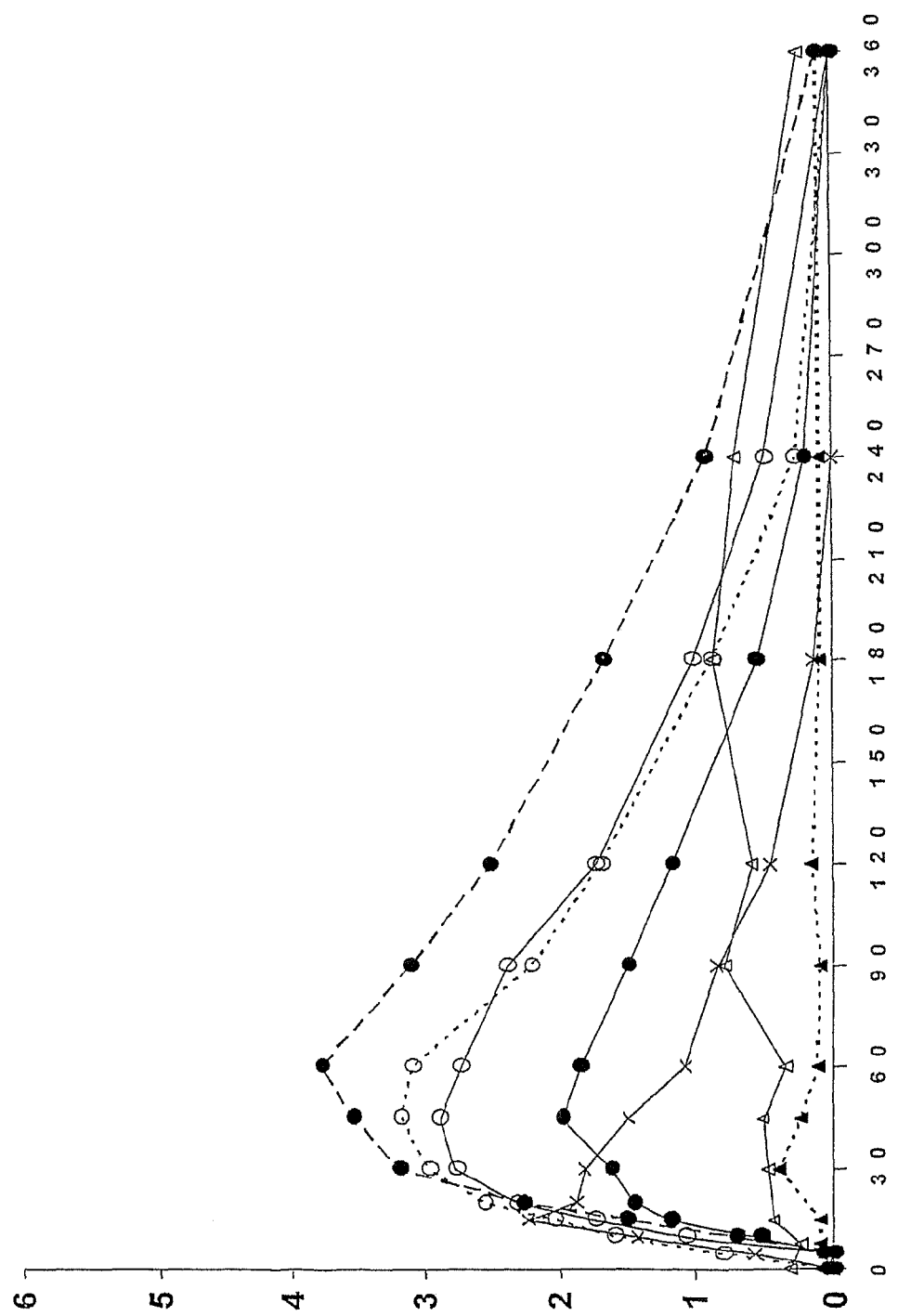

PHARMACEUTICAL FORMULATION OF APOMORPHINE FOR BUCCAL ADMINISTRATION

This application is a Continuation application of U.S. application Ser. No. 11/919,799, filed Nov. 2, 2007; which is a 371 of PCT/GB2006/001665, filed May 8, 2006, the entire contents of which are incorporated herein by reference.

FIELD OF THE INVENTION

The present invention relates to pharmaceutical formulations of apomorphine, a drug used in the management of Parkinson's disease and in the treatment of sexual dysfunction. More specifically the invention relates to pharmaceutical formulations of apomorphine which are for buccal administration.

BACKGROUND OF THE INVENTION

Parkinson's disease is a chronic, progressive neurological disorder affecting approximately 20 in every 100,000 people. The disease is typically characterised by resting tremor, muscle rigidity, bradykinesia and postural instability. Although the exact pathological course of Parkinson's disease is unknown, the dopaminergic neurones in the substantia nigra are progressively destroyed which leads to a net decrease in the amount of dopamine in the basal ganglia. Dopamine replacement with levodopa is the current primary therapy for Parkinson's disease.

After a three to five year period of control, 25% of Parkinson's disease sufferers develop "on-off" fluctuations. These are characterised by periods of a few minutes to a few hours during which the patient is able to move and walk easily ("on"), alternating with periods during which the patient experiences severe akinesia ("off"). Many patients also experience other unpleasant "off" period phenomena, such as depression, anxiety, panic, pain, delusions and dystonia, which follow a time-course parallel to the motor stage. The "off" periods may appear several times a day even when anti-parkinsonian drugs are given at the optimum dosage.

Dopamine agonists have been shown to decrease dyskinesias and "on-off" fluctuations when combined with levodopa therapy. Apomorphine is a non-ergot dopamine agonist which has a high affinity for $D_2$, $D_3$ and $D_4$ and lower affinity for $D_1$, and $D_5$ receptors. It has the following structural formula:

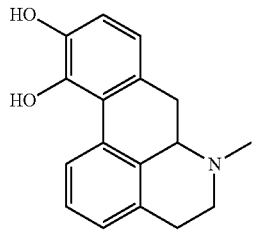 [SMILES: CN1CCc2cccc3c2C1Cc1ccc(O)c(O)c1-3]

Oral doses in excess of 500 mg apomorphine have been shown to produce a dose-dependent improvement in tremor, rigidity, and akinesia but are associated with drug-induced nephrotoxicity. This is thought to be a result of nephrotoxic metabolites produced by the liver, presumably due to extensive first-pass metabolism.

Subcutaneous injections of apomorphine have proved to be effective in the treatment of "on-off" fluctuations in Parkinson's disease within 5 to 15 minutes, and last for 45 to 90 minutes. Trials have shown consistent reversal of "off" period akinesia, a decrease in daily levodopa requirements and consequently a decrease in the amount of "on" period dyskinesias. Advantages over other dopamine agonists include a quick onset of action and lower incidence of psychological complications. For a "rescue therapy" in patients with "on-off" fluctuations, apomorphine also has the advantage over other dopamine agonists that it has a relatively short half-life.

As there is a large inter-subject variation in pharmacokinetics, patients undergo an initial dose titration period at the start of treatment. Nausea and vomiting which may occur as a result of the peripheral dopaminergic action of apomorphine may be controlled by domperidone. Often, patients on long-term apomorphine treatment are able to discontinue or decrease the dose of domperidone without recurrence of these adverse effects.

The widespread application of apomorphine to control "on-off" fluctuations is limited by the necessity for subcutaneous administration. Alternative routes of administration have consequently been investigated. Intranasal apomorphine was shown to be effective in patients with Parkinson's disease but produced transient nasal blockage and burning sensation in two of five patients tested. Rectal administration of apomorphine has been shown to be effective and to have a longer duration of action than subcutaneously administered drug; however, higher doses of the drug are needed because of some first-pass metabolism. Furthermore, the delayed onset of action limits its application as a supplemental dopamine agonist therapy.

Sublingual administration of apomorphine has also been studied. Minimal first-pass metabolism allows for the use of lower doses compared with standard oral administration of apomorphine. In all studies, all patients (who were known to be responsive to subcutaneous apomorphine) fully "switched on". The mean time to onset of effect was approximately 30 minutes and was comparable between the studies. The mean duration of action was longer following sublingual administration compared to subcutaneous administration. Unpleasant taste and inconsistency of dissolution were noted formulation problems.

The use of apomorphine in treating sexual dysfunction has also been investigated. For instance, the sublingual administration of apomorphine has been found in a clinical study to have a statistically significant effect on erectile dysfunction when compared with placebo (Dula et al Urology 2000; 56: 130-135). According to the literature, apomorphine promotes sexual function and performance because of the effect it exerts on the brain, in particular on the neurological mechanisms underlying sexual arousal. Apomorphine can thus be used to promote or enhance sexual function, treat sexual dysfunction, enhance libido and/or reduce impotence.

For optimal buccal absorption the apomorphine used should ideally be un-ionised at physiological pH. The $pK_a$ of apomorphine is 8.9 so, above a pH of about 9, significant amounts of the drug exist as (free base. Thus at pH 3.5 the proportion of apomorphine which is un-ionised is negligible. The proportion of drug which is un-ionised only starts to increase when the pH approaches 7; an alkaline pH yields increasing proportions of un-ionised drug. Thus, for optimal absorption, the drug should be formulated in an alkaline medium.

Apomorphine undergoes rapid spontaneous oxidation. One way to prevent this is to keep solutions of the drug acidified. It is believed that commercially-available apomorphine for injection has a pH of about 3.5. Since this is intended for injection the pH does not influence systemic absorption. However, the nasal spray formulation described above is also an aqueous solution and is also believed to be acidic. This would imply that the formulation is not optimised for nasal absorption and the nasal irritation that has been reported might well derive from the acidic property of the formulation.

Administration of acidic apomorphine formulations into the mouth results in a stimulation of salivation. The excess saliva produced is rich in bicarbonate, which is intended to neutralise the acid and return the mouth to its normal, near neutral, pH. Although the resultant increase in pH should aid the absorption of apomorphine, there is also an increase in the amount of drug swallowed along with the additional volume of saliva. As a result, the amount of drug available for buccal absorption rapidly decreases.

SUMMARY OF THE INVENTION

The present invention aims to overcome these and other problems associated with formulating apomorphine for delivery in the mouth. Its objective is to achieve an immediate use preparation of the drug which is optimised for buccal administration. Accordingly, the present invention provides:

A kit comprising, in separate compartments of a container, the following components:
  (a) a combination of apomorphine or a pharmaceutically acceptable acid addition salt thereof and a pharmaceutically acceptable excipient or carrier; and
  (b) a solution which comprises a diluent and a pH modifying agent;
the components being presented such that they can be combined at the point of use into a formulation which is adjusted to a pH ranging from mildly acidic to alkaline and which is suitable for buccal administration.

A process for producing a pharmaceutical composition, which process comprises combining apomorphine or a pharmaceutically acceptable acid addition salt thereof with a solution comprising a diluent and a pH modifying agent such that the resulting formulation is adjusted to a pH ranging from mildly acidic to alkaline and is suitable for buccal administration.

Use of apomorphine or a pharmaceutically acceptable acid addition salt thereof, and a solution comprising a diluent and a pH modifying agent, in the manufacture of a medicament which is adjusted to a pH ranging from mildly acidic to alkaline and which is formulated for buccal delivery to a patient.

Use of apomorphine or a pharmaceutically acceptable acid addition salt thereof, and a solution comprising a diluent and a pH modifying agent, in the manufacture of a medicament which is adjusted to a pH ranging from mildly acidic to alkaline and which is formulated for buccal delivery to a subject, the medicament being for treating Parkinson's disease or for promoting sexual function, treating sexual dysfunction, enhancing libido or reducing impotence.

BRIEF DESCRIPTION OF THE FIGURE

FIG. 1 is a graph of plasma concentration of apomorphine (y axis) in units of ng/ml, against time (x axis) in units of minutes, in which:
  x relates to Formulation 1 of the invention (2.5 apomorphine dose);
  • on a continuous line relates to the 5 mg apomorphine dose formulation of WO97/06786;
  ○ on a continuous line relates to the 10 mg apomorphine dose formulation described in Table I and FIG. 1 of WO97/06786;
  ○ on a dotted line relates to the 10 mg apomorphine dose formulation described in Table II and FIG. 2 of WO97/06786;
  • on a dashed line relates to the 20 mg apomorphine dose formulation described in WO97/06786;
  ▲ relates to the 4 mg apomorphine dose formulation described in WO99/66916; and
  Δ relates to the 8 mg apomorphine dose formulation described in WO99/66916.

DETAILED DESCRIPTION OF THE INVENTION

The apomorphine in component (a) is present as the free base or as a pharmaceutically acceptable acid addition salt. Suitable salts include salts of inorganic acids such as hydrochloric acid, hydrobromic acid and sulphuric acid.

Component (a) is present in any suitable form. In one embodiment it is in particulate form, for instance dry particulate form. In another embodiment it is present in suspension or liquid form. For example, component (a) may be present as a powder or granules, such as a dry powder or dry granules. It may alternatively be present as a suspension of powder or granules in an appropriate suspension medium, or dissolved in liquid form in a solvent liquid. The suspension medium or solvent liquid may be water, for example.

Component (a) comprises a pharmaceutically acceptable excipient or carrier. Examples of suitable excipients include solubilisers (to aid solubility of the active agent), antioxidants (to prevent oxidation of the active agent) and adhesive agents (to prolong buccal retention) and suitable dry powder bulking agents employed in standard pharmaceutical preparations or standard solvents capable of forming a stable solution or suspension of apomorphine as the free base or pharmaceutically acceptable acid addition salt. This component is stored in an appropriate container separately from component (b).

Component (b) is a solution comprising a diluent and a pH modifying agent. In this context, a pH modifying agent is an agent which is capable of modifying the pH of a solution to achieve a desired pH. The pH modifying agent serves to regulate the pH of the formulation which results from combining components (a) and (b) at the point of use. The pH modifying agent should thus be capable of achieving a pH ranging from mildly acidic to alkaline, for instance a pH of from 5 to 10, typically from 6 to 10 and more preferably from 6 to 9, or 7 to 9, for example about 6, about 7 or about 8. The pH modifying agent is pharmaceutically acceptable. Any suitable pH modifying agent may be used, for instance a base, an alkali or a buffer. The base may be any suitable base, for instance a carbonate or hydrogen carbonate salt, such as an alkali metal or alkaline earth metal carbonate or an alkali metal or alkaline earth metal hydrogen carbonate; a metal hydroxide, for instance an alkali metal hydroxide or an alkaline earth metal hydroxide; or a metal oxide, for instance an alkali metal oxide or an alkaline earth metal oxide. The alkali may be any suitable alkali, for instance a carbonate, hydroxide or other basic ionic salt of an alkali metal or alkaline earth metal. Typically, the base or the alkali is a hydroxide of an alkali metal or alkaline earth metal. More typically, the base or alkali is an alkali metal hydroxide such as sodium hydroxide or potassium hydroxide.

The pH modifying agent is typically a buffer. In this context a buffer is any solution, or compound that forms a solution with the diluent of component (b), which is capable of resisting change in pH, for example upon addition of acid or base or upon dilution. The buffer should be capable of achieving a pH ranging from mildly acidic to alkaline, for instance a pH of from 5 to 10, typically from 6 to 10 and more preferably from 6 to 9, or 7 to 9, for example about 6, about 7 or about 8. The buffer may be any suitable buffer, for instance a phosphate salt such as an alkali metal phosphate. Suitable examples of phosphate salts include sodium phosphate and potassium phosphate. Other suitable buffers include: disodium hydrogen phthalate and sodium dihydrogen orthophosphate; dipotassium hydrogen phthalate and potassium dihydrogen orthophosphate; and sodium tetraborate and hydrochloric acid. The buffer is typically present in an amount of from 0.02 to 10% by weight.

The diluent of component (b) may be any suitable diluent, for instance water, a polar organic solvent, a mixture of water and a polar organic solvent or any aqueous solvent. Typically, the polar organic solvent is one which is miscible with water. The polar organic solvent may be a polar protic solvent. The polar protic solvent may be an alcohol, such as ethanol. Alternatively, the solvent may be polyethylene glycol. Typically, the diluent comprises water. More typically the diluent is water. In a preferred embodiment the solution which is component (b) is an aqueous solution.

Component (b) may further include one or more additional pharmaceutically acceptable excipients, examples of which include solubilisers (to aid solubility of the active agent), flavouring agents, antioxidants (to prevent oxidation of the active agent) and adhesive agents (to prolong buccal retention). Typically, a unit of component (b) contains from 0.1 to 5 ml of the diluent, for instance 0.1 to 2 ml of the diluent. Typically the diluent is water, and a unit amount of component (b) contains from 0.1 to 5 ml of water, for instance from 0.1 to 2 ml of water.

In one embodiment, component (b) is an aqueous solution comprising water and a buffer. Accordingly the invention further provides a kit comprising, in separate compartments of a container, the following components:
 (a) a combination of apomorphine or a pharmaceutically acceptable acid addition salt thereof and a pharmaceutically acceptable excipient or carrier; and
 (b) an aqueous solution which comprises water and a buffer; the components being presented such that they can be combined at the point of use into a formulation which is adjusted to a pH ranging from mildly acidic to alkaline and which is suitable for buccal administration.

In the kit of the invention defined in the preceding paragraph, the buffer serves to regulate the pH of the formulation which results from combining components (a) and (b) at the point of use. The buffer should thus be capable of achieving a pH ranging from mildly acidic to alkaline, for instance a pH of from 5 to 10, typically from 6 to 10 and more preferably from 6 to 9, or 7 to 9, for example about 6, about 7 or about 8. The buffer may be any suitable buffer, for instance a phosphate salt such as an alkali metal phosphate. Suitable examples of phosphate salts include sodium phosphate and potassium phosphate. The buffer is typically present in an amount of from 0.02 to 10% by weight. Component (b) may further include one or more additional pharmaceutically acceptable excipients, examples of which include solubilisers (to aid solubility of the active agent), flavouring agents, antioxidants (to prevent oxidation of the active agent) and adhesive agents (to prolong buccal retention). A unit amount of component (b) contains from 0.1 to 5 ml of water, for instance 0.1 to 2 ml of water.

In the kit of the present invention, the container holding components (a) and (b) comprises at least two compartments and is typically a drug delivery device of conventional structure. The two components are mixed together at the time of use and the resulting formulation is administered to a patient via the buccal route. Preferably the formulation is administered immediately after the mixing together of the two components.

The formulated apomorphine product, obtained after mixing components (a) and (b), is mildly acidic, neutral or slightly alkaline, preferably slightly alkaline, in order to promote rapid absorption. This represents an advantage over existing formulations of apomorphine, which are acidified to preserve stability but which are consequently not optimised for buccal administration.

The present invention provides a means of formulating apomorphine in such a way that it is optimised for buccal administration and rapid absorption whilst being sufficiently stable to prevent auto-oxidation. This is particularly important because "on-off" phenomena in Parkinson's disease can occur very rapidly. The key to an effective rescue treatment is thus speed of absorption and hence speed of action of the active agent.

If the pH of the product is adjusted to about 8.0, approximately 10% of the apomorphine becomes un-ionised and thus available for absorption. The pH-dependent degree of ionisation of the drug is maintained by a dynamic equilibrium. As un-ionised drug is removed by absorption, more ionised drug becomes un-ionised in order to restore the equilibrium. As a result there is always a sufficient amount of un-ionised drug generated that can be absorbed rapidly.

It is important that the formulation of the present invention be optimised for buccal administration and rapid absorption. The formulation may therefore include additional agents, for instance solubilising agents that enhance the solubility of apomorphine whilst also promoting buccal absorption, and adhesive agents to help prevent loss of the drug by swallowing.

The combination of apomorphine or a pharmaceutically acceptable salt thereof and a pharmaceutically acceptable excipient or carrier is typically prepared following conventional methods. It is provided in any suitable form, for instance as a dispersible powder or granules, as a suspension, or in liquid form. The combination may contain one or more additional agents, for instance selected from sweetening agents, flavouring agents, colouring agents and preserving agents in order to provide a pharmaceutically elegant and palatable preparation.

In the combination which forms component (a) of the kit of the present invention, the non-toxic pharmaceutically acceptable excipient or carrier is any which is known to be suitable for the manufacture of powders, tablets, granules, suspensions or solutions. Such excipients or carriers may be, for example, inert diluents such as calcium carbonate, sodium carbonate, lactose, dextrose, saccharose, cellulose, corn starch, potato starch, calcium phosphate or sodium phosphate; granulating or disintegrating agents, for example, maize starch, alginic acid, alginates or sodium starch glycolate; binding agents, for example starch, gelatin or acacia; lubricating agents, for example silica, magnesium or calcium stearate, stearic acid or talc; dyestuffs; or sweeteners. Additional agents that may be included in component (a) include solubilising agents, for instance a poloxamer or sodium lauryl sulphate; a preservative, for instance an antioxidant such as ascorbic acid (vitamin C) or α-tocopherol; a thickening agent, for instance polyvinyl alcohol; a bulking agent such as xylitol, lactose or mannitol; or a flavouring or sweetening agent such as sucrose, sorbitol or saccharin.

When component (a) of the kit is in the form of a suspension, it is present in a suitable suspension medium or in the form of a solution in a suitable solvent. The suspension medium or solvent may be water, for example. Additional agents, as above, may be included in these forms of component (a). Such excipients or carriers may be, for example, inert solvents with buffering salts to enhance stability and/or solubilising agents and/or suspending agents.

The solution which is component (b) of the kit of the present invention may contain, in addition to the diluent and the pH modifying agent, one or more excipients known to be suitable for the manufacture of solutions or suspensions. Typically, the solution which is component (b) is an aqueous solution in which the diluent comprises water, or is water, and the one or more excipients are selected from those known to be suitable for the manufacture of aqueous solutions or suspensions. Such excipients include preservatives, for example an antioxidant such as ascorbic acid (vitamin C), α-tocopherol, or ethyl or n-propyl p-hydroxybenzoate; a co-solvent such as aqueous ethanol; a thickening agent such as polyvinyl alcohol; or a flavouring or sweetening agent such as those mentioned above for component (a). A formulation for diabetic patients may include only ingredients, for example sorbitol, which do not metabolise to glucose or which only metabolise a very small amount to glucose.

In one embodiment of the kit of the present invention, the solution which is component (b) is an aqueous solution comprising water, a buffer and one or more excipients known to be suitable for the manufacture of aqueous solutions or suspensions. Such excipients include those referred to in the preceding paragraph.

The formulation of the present invention typically delivers from 0.05 mg to 40 mg of apomorphine (as free base or salt) per unit dose.

Examples of typical ingredients, and their relative amounts, in components (a) and (b) are listed below:

Component (a) in Powder State
    A pomorphine: 0.05 mg-40 mg per unit dose
    Poloxamer: 0.0 to 5% w/w (solubilising agent)
    Sodium lauryl sulphate: 0.0 to 5% w/w (solubilising agent)
    Alpha-tocopherol: 0.0 to 2.0% w/w (preservative))
    Microbiological preservative: 0.0 to 2.0% w/w
    Polyvinyl Alcohol: 0.0 to 5% w/w (thickening agent)
    Flavouring: 0.0 to 4.00% w/w
    Artificial sweetener: 0.0 to 4.00% w/w
    Natural sweetener: 0.0 to 8.00% w/w
    Xylitol qs Bulk mix:—bulking agent
    Lactose qs Bulk mix:—bulking agent
    Mannitol qs Bulk mix:—bulking agent Component (a) in solution or suspension state
    Apomorphine: 0.05 mg-40 mg per unit dose
    Water qs: 0.1 to 2 ml (vehicle)
    Phosphate Salts: 0.02 to 10% w/w (buffer)
    Citrate Salts: 0.02 to 10% w/w (buffer)
    NaOH/HCl qs: to pH 2 to 7
    Flavouring: 0.005 to 4.00% w/w
    Artificial Sweetener: 0.005 to 4.00% w/w
    Natural Sweetener: 0.005 to 8.00% w/w
    Poloxamer: 0.05 to 5% w/w (solubilising agent)
    Sodium Lauryl Sulphate: 0.05 to 5% w/w (solubilising agent)
    Other solubilising agents: 0.05 to 5% w/w
    Alcohol: 0 to 15% w/v (co-solvent)
    Alpha-tocopherol
    (or alternative): 0.02 to 2.0% w/w (preservative)
    Microbiological preservative: 0.02 to 2.0% w/w (preservative)
    Polyvinyl Alcohol: 0.05 to 5% w/w (thickening agent)
    Agar gum 0.05 to 10.0% w/w/(suspending agent)
    (or alternative)

Component (b)
    Water qs: 0.1 to 2 ml (vehicle)
    Phosphate Salts: 0.02 to 10% w/w (buffer)
    NaOH/HCl qs: to pH 5 to 10
    Flavouring: 0.005 to 4.00% w/w
    Artificial Sweetener: 0.005 to 4.00% w/w
    Natural Sweetener: 0.005 to 8.00% w/w
    Poloxamer: 0.05 to 5% w/w (solubilising agent)
    Sodium Lauryl Sulphate: 0.05 to 5% w/w (solubilising agent)
    Other solubilising agents: 0.05 to 5% w/w
    Alcohol: 0 to 15% w/v (co-solvent)
    Alpha-tocopherol
    (or alternative): 0.02 to 2.0% w/w (preservative)
    Microbiological preservative: 0.02 to 2.0% w/w (preservative)
    Polyvinyl Alcohol: 0.05 to 5% w/w (thickening agent)

Components (a) and (b) as described above are combined at the point of use into a formulation which is adjusted to a pH ranging from mildly acidic to alkaline and which is suitable for buccal administration. A pharmaceutical composition may thus be prepared by a process which comprises combining apomorphine or a pharmaceutically acceptable acid addition salt thereof with a solution which comprises a diluent and a pH modifying agent, such that the resulting formulation is adjusted to a pH ranging from mildly acidic to alkaline and is suitable for buccal administration.

In one embodiment of this process, the solution is an aqueous solution, the diluent is water and the pH modifying agent is a buffer. Accordingly, the present invention further provides a process for producing a pharmaceutical composition, which process comprises combining apomorphine or a pharmaceutically acceptable acid addition salt thereof with an aqueous solution comprising water and a buffer such that the resulting formulation is buffered to a pH ranging from mildly acidic to alkaline and is suitable for buccal administration.

Components (a) and (b) as described above may be used in the manufacture of a medicament which is adjusted to a pH ranging from mildly acidic to alkaline and which is formulated for buccal delivery to a patient. Accordingly, the present invention provides the use of apomorphine or a pharmaceutically acceptable acid addition salt thereof, and a solution comprising a diluent and a pH modifying agent, in the manufacture of a medicament which is adjusted to a pH ranging from mildly acidic to alkaline and which is formulated for buccal delivery to a patient.

In one embodiment of this use, the solution is an aqueous solution, the diluent is water and the pH modifying agent is a buffer. Accordingly, the present invention further provides the use of apomorphine or a pharmaceutically acceptable acid addition salt thereof, and an aqueous solution comprising water and a buffer, in the manufacture of a medicament which is buffered to a pH ranging from mildly acidic to alkaline and which is formulated for buccal delivery to a patient.

Components (a) and (b) as described above may also be used in the manufacture of a medicament which is adjusted to a pH ranging from mildly acidic to alkaline and which is formulated for buccal delivery to a patient, the medicament being for treating Parkinson's disease or for promoting sexual function, treating sexual dysfunction, enhancing libido or reducing impotence. Accordingly, the present invention provides the use of apomorphine or a pharmaceutically acceptable acid addition salt thereof, and a solution comprising a diluent and a pH modifying agent, in the manufacture of a medicament which is adjusted to a pH ranging from mildly acidic to alkaline and which is formulated for buccal delivery to a subject, the medicament being for treating Parkinson's disease or for promoting sexual function, treating sexual dysfunction, enhancing libido or reducing impotence.

In one embodiment of this use, the solution is an aqueous solution, the diluent is water and the pH modifying agent is a buffer. Accordingly, the present invention further provides the use of apomorphine or a pharmaceutically acceptable acid addition salt thereof, and an aqueous solution comprising water and a buffer, in the manufacture of a medicament which is buffered to a pH ranging from mildly acidic to alkaline and which is formulated for buccal delivery to a subject, the medicament being for treating Parkinson's disease or for promoting sexual function, treating sexual dysfunction, enhancing libido or reducing impotence.

The invention will be further described in the Examples which follow:

Example 1

Preparation of a Formulation of the Invention

A commercially available injectable solution of apomorphine in hydrochloric acid with a pH of 3.5 (trade name "APO-go", supplied by Britannia Pharmaceuticals) was employed as component (a). A solution of sodium hydroxide was employed as component (b).

A pre-calculated amount of sodium hydroxide was added to a solution of APO-go in order to bring the pH of the solution up to 6. The resulting mixture was put into a vortex blender. Subsequently, the blended mixture was drawn up into a syringe ready for squirting onto a patient's tongue.

Example 2

Pharmacokinetic Study

The objective of this study was to investigate the bioavailability of apomorphine hydrochloride following administration, to 12 healthy volunteers by the oral route, of a formulation which could be prepared using a two-compartment kit of the present invention. Formulation 1 was used, which was prepared, according to Example 1, individually for each volunteer in turn.

Due to the emetic properties of apomorphine, subjects were pre-treated with the anti-emetic domperidone. Following 2 days of domperidone pre-treatment, Formulation 1 was prepared as described in Example 1 for each volunteer in turn. Subjects received a 2.5 mg dose of apomorphine by administration of Formulation 1 by the sub-lingual route: in each case the solution was made up and drawn into a syringe as described in Example 1, and then squirted onto the volunteer's tongue. Blood samples for pharmacokinetic analysis were taken pre-dose and at intervals for 6 hours after each dose of apomorphine. Assessment of the bioavailability of apomorphine was made using the pharmacokinetic parameters $C_{max}$ and AUC (area under the plasma apomorphine concentration-time curve).

This study was similar to that described in WO 97/06786, which describes oral fast-dissolving compositions for dopamine agonists, and in WO 99/66916, which describes apomorphine-containing dosage forms for ameliorating male erectile dysfunction. It should be noted that the formulation used in WO 97/06786 was adjusted to pH 3.0 (whereas in Formulation 1, the solution was adjusted to pH 6.0), and that the formulation in WO 99/66916 was not pH-adjusted, but intended to release the drug slowly.

The bioavailabities of the formulations of apomorphine given by the buccal route were either extracted from WO 97/06786 and WO 99/66916 or were estimated from the data contained therein (shown in italics), and compared with a dose of 2.5 mg apomorphine in Formulation 1 (see Table I and FIG. 1). After correction for the administered dose, administration of 2.5 mg apomorphine as Formulation 1 resulted in a disproportionately high bioavailability (Table This result is consistent with the immediate availability of the drug for absorption (due to administration of a solution of apomorphine; as opposed to the slow-release of the formulation described in WO 99/66916) and supports that a higher pH formulation results in higher bioavailability (as demonstrated by a direct comparison of the pH 3.0 formulation described in WO 97/06786 and Formulation 1 which is adjusted to pH 6.0).

TABLE I

Bioavailability of apomorphine given by buccal administration (Mean values).

| Dosage group (apomorphine dose) | $C_{max}$ (ng/ml) | AUC ng · h/ml |
|---|---|---|
| Formulation 1 (2.5 mg) | 2.60 | 213.75 |
| WO 97/06786 (5 mg) | 1.9 | 337.6 |
| WO 97/06786 (10 mg; see FIG. 1 of WO 97/06786) | 2.9 | 504.8 |
| WO 97/06786 (10 mg; see FIG. 2 of WO 97/06786) | 3.2 | 402.2 |
| WO 97/06786 (20 mg) | 3.8 | 690.1 |
| WO 99/66916 (4 mg) | 0.39 | 45.1 |
| WO 99/66916 (8 mg) | 0.87 | 211.2 |

TABLE II

Dose-corrected bioavailability of apomorphine given by buccal administration (Mean values).

| Dosage group | $C_{max}$ (ng/ml/mg) | AUC (ng · h/ml/mg) |
|---|---|---|
| Formulation 1 | 1.04 | 85.50 |
| WO 97/06786 | 0.31 | 40.22 |
| WO 99/66916 | 0.17 | 28.62 |

The invention claimed is:

1. A method of buccally administering an apomorphine composition to a patient in need thereof, comprising:
   (a) at the time of administration, adding a diluent and a pH modifying agent to an apomorphine composition to form a liquid composition comprising a pharmaceutically effective amount of apomorphine or a pharmaceutically acceptable acid addition salt thereof and a pharmaceutically acceptable excipient or carrier and to adjust the pH of the liquid composition to a pH ranging from mildly acidic to alkaline, thereby forming a pH adjusted liquid composition; and then
   (b) introducing the resulting pH adjusted liquid composition to the mouth of a patient in need thereof, thereby buccally administering a pharmaceutically effective amount of apomorphine or a pharmaceutically acceptable acid salt thereof.

2. The method of claim 1, wherein the diluent comprises water.

3. The method of claim 1, wherein the pH modifying agent comprises a buffer effective for buffering the composition to a pH ranging from mildly acidic to alkaline.

4. The method of claim 1, wherein composition is administered to treat Parkinson's disease.

5. The method of claim 1, wherein the composition is administered to promote function, treat sexual dysfunction, enhance libido, reduce impotence, or a combination thereof.

* * * * *